United States Patent [19]
Justin et al.

[11] Patent Number: 5,505,733
[45] Date of Patent: Apr. 9, 1996

[54] INTRAMEDULLARY SKELETAL DISTRACTOR AND METHOD

[76] Inventors: Daniel F. Justin, 4544 Trescott Dr., Orlando, Fla. 32817; J. Dean Cole, 500 Lakeview St., Orlando, Fla. 32804

[21] Appl. No.: 141,242

[22] Filed: Oct. 22, 1993

[51] Int. Cl.⁶ .......................... A61B 17/56; A61B 17/66; A61B 17/72
[52] U.S. Cl. .................. 606/63; 606/62; 606/68; 606/105; 192/48.92; 74/89.15
[58] Field of Search .................. 192/48.92, 45; 606/53, 54, 60–68, 105; 74/89.45, 586

[56] References Cited

U.S. PATENT DOCUMENTS

| | | | |
|---|---|---|---|
| 3,194,368 | 7/1965 | Benson et al. | 192/45 |
| 3,528,534 | 9/1970 | Benson et al. | 192/45 |
| 3,990,555 | 11/1976 | Carullo | 192/45 |
| 4,016,874 | 4/1977 | Maffei et al. | 606/62 |
| 4,135,507 | 1/1979 | Harris | 606/64 X |
| 4,827,917 | 5/1989 | Brumfield | 606/64 |
| 4,858,602 | 8/1989 | Seidel et al. | 606/64 X |
| 4,875,475 | 8/1989 | Comte et al. | 606/64 |
| 4,946,459 | 8/1990 | Bradshaw et al. | 606/63 |
| 5,034,013 | 7/1991 | Kyle et al. | 606/62 |
| 5,035,697 | 7/1991 | Frigg | 606/67 |
| 5,074,882 | 12/1991 | Grammont et al. | 623/23 |
| 5,108,398 | 4/1992 | McQueen et al. | 606/105 X |
| 5,112,333 | 5/1992 | Fixel | 606/63 X |
| 5,122,141 | 6/1992 | Simpson et al. | 606/63 X |
| 5,263,955 | 11/1993 | Baumgart et al. | 606/63 |
| 5,268,000 | 12/1993 | Ottieri et al. | 606/63 X |
| 5,350,379 | 9/1994 | Spievack | 606/63 |

FOREIGN PATENT DOCUMENTS

| | | | |
|---|---|---|---|
| 0547380 | 6/1993 | European Pat. Off. | 606/67 |
| 2224214 | 11/1973 | Germany | 606/63 |
| 2246274 | 3/1974 | Germany | 606/64 |
| 2705154 | 8/1978 | Germany | 606/64 |
| 0385580 | 6/1973 | U.S.S.R. | 606/62 |

OTHER PUBLICATIONS

37th Annual Meeting, Orthopaedic Research Society, Mar. 4–7, 1991.
"Diaphyseal Lengthening System", Medinov, The Innovation Orthopaedics.

*Primary Examiner*—Robert A. Hafer
*Assistant Examiner*—Brian E. Hanlon
*Attorney, Agent, or Firm*—Allen, Dyer, Doppelt, Franjola & Milbrath

[57] ABSTRACT

A device for effecting progressive elongation of a sectioned bone having no extracutaneous elements, and a method for using the device, are presented. The device, which includes a pair of telescopically engaged cylindrical members, is inserted into the medullary space of the bone, and one cylindrical member is affixed to each section of bone. Under the normal torsions experienced by the affected limb, a clutch mechanism is provided that causes the cylindrical members to be forced apart, separating the sections of bone, at which site new bone growth is stimulated. Rotations as small as 1 degree are sufficient to activate elongation. In order to limit excessive rotational displacement, a keyring mechanism is provided that limits rotation to that which is physically tolerated yet provides sufficient lengthening, typically between 3 and 5 degrees. In order that excessive separation of the cylindrical members not occur, an indicator mechanism is further provided that prevents elongation beyond a predetermined amount per unit time. The indicator mechanism can be overcome by forcible external manipulation so that a new cycle of elongation may begin.

18 Claims, 6 Drawing Sheets

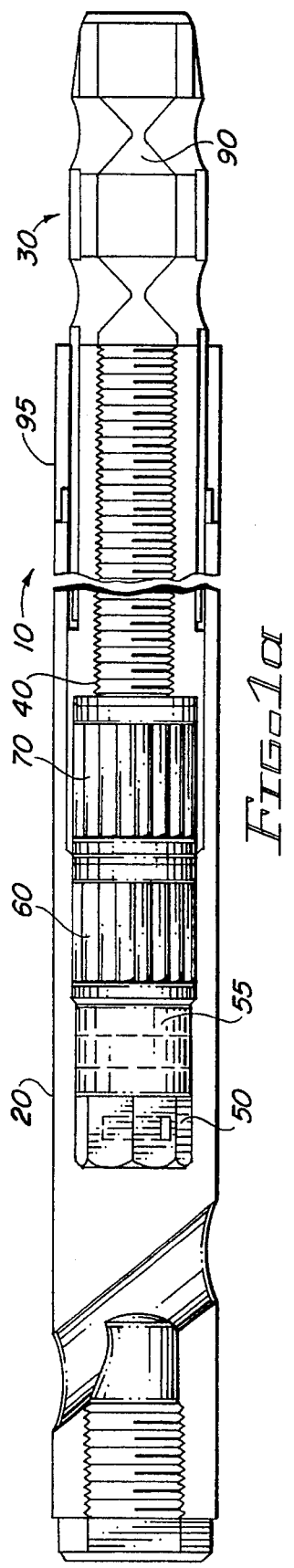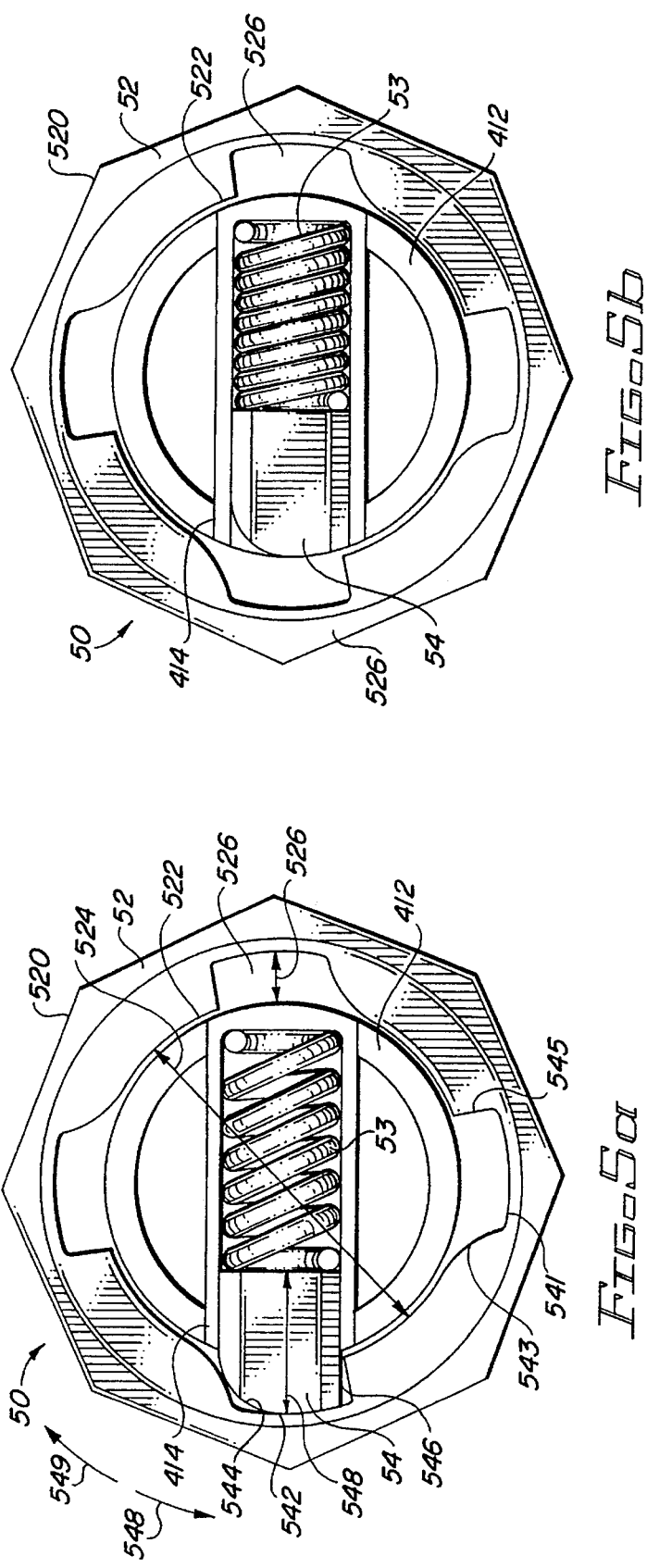

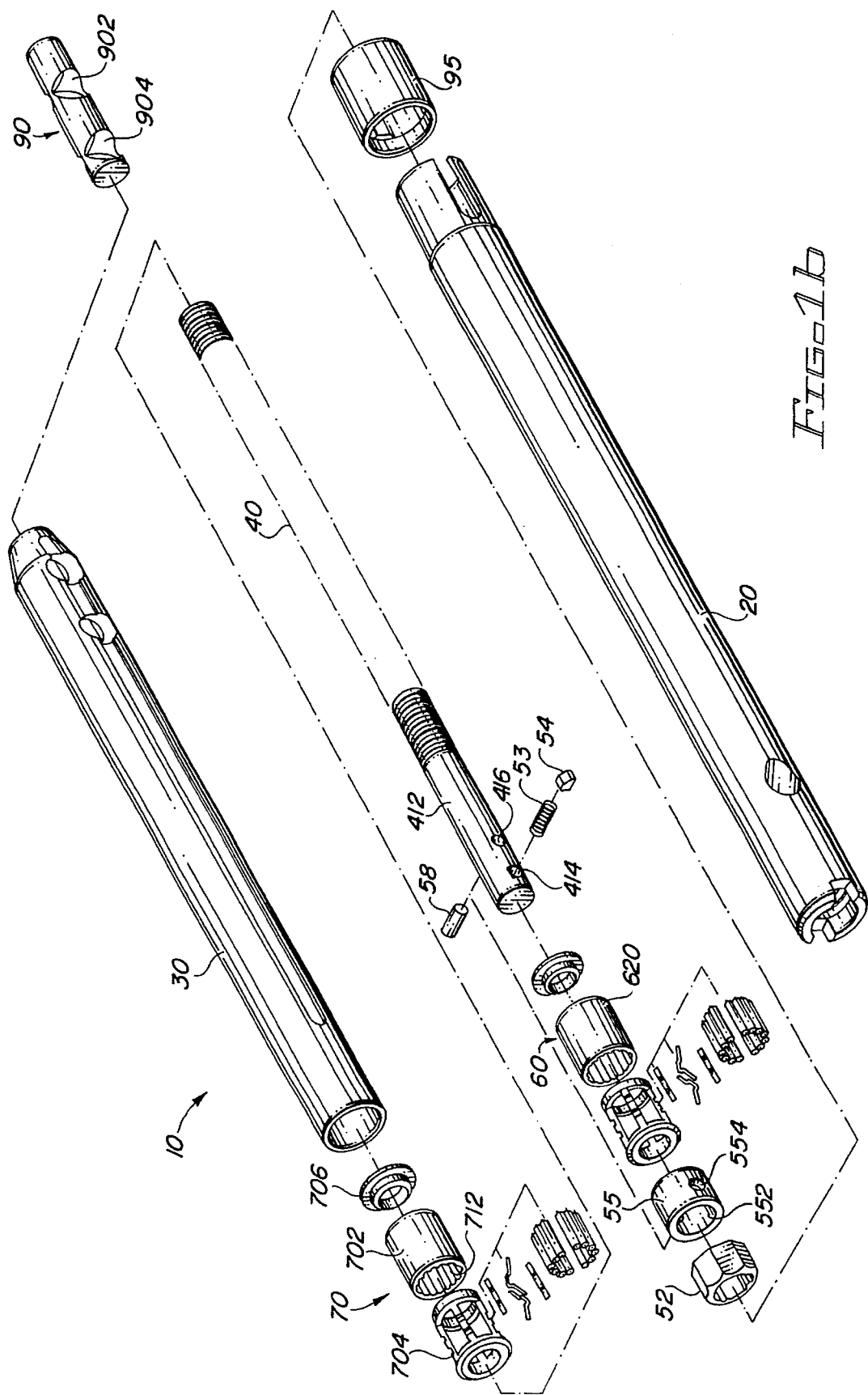

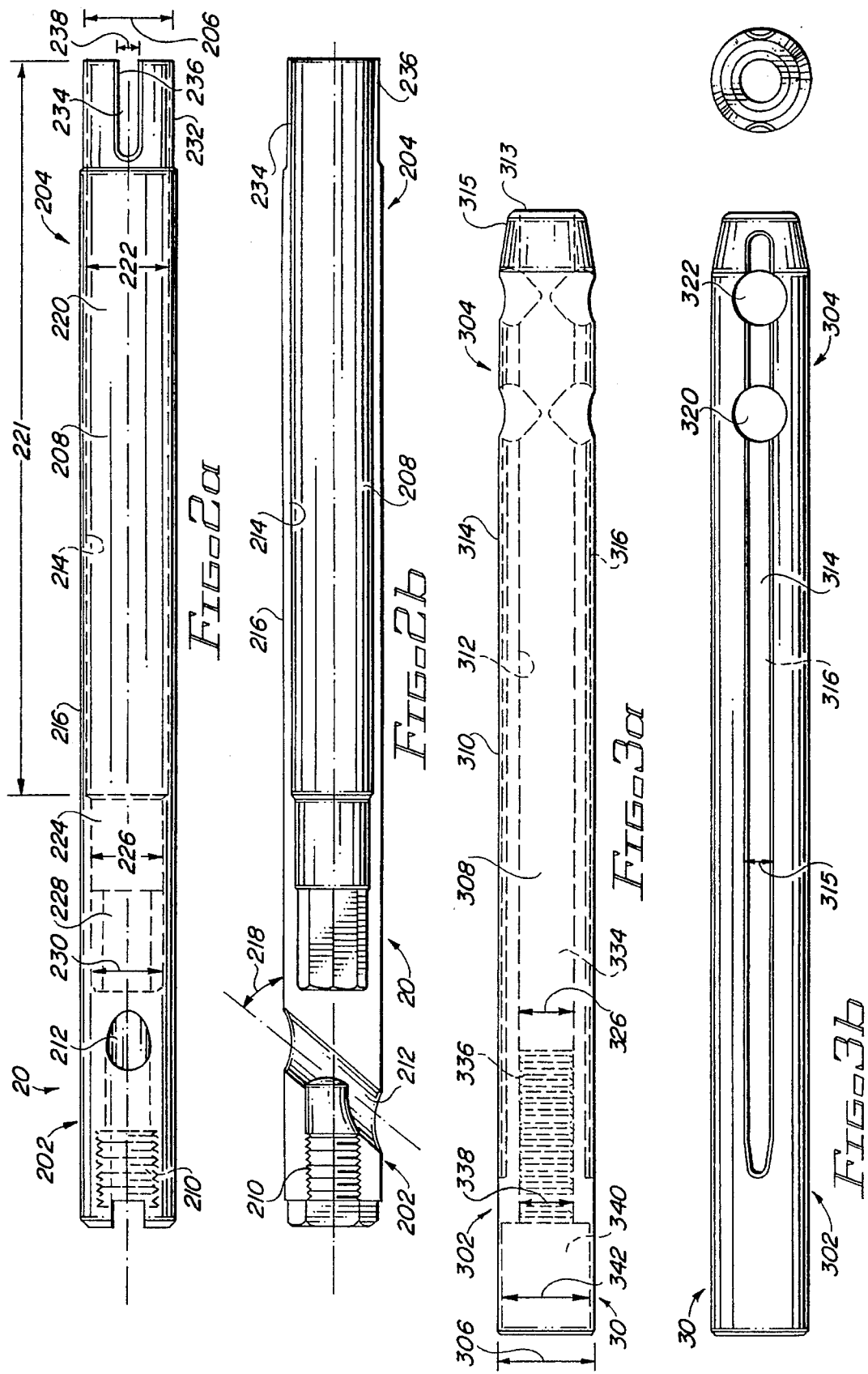

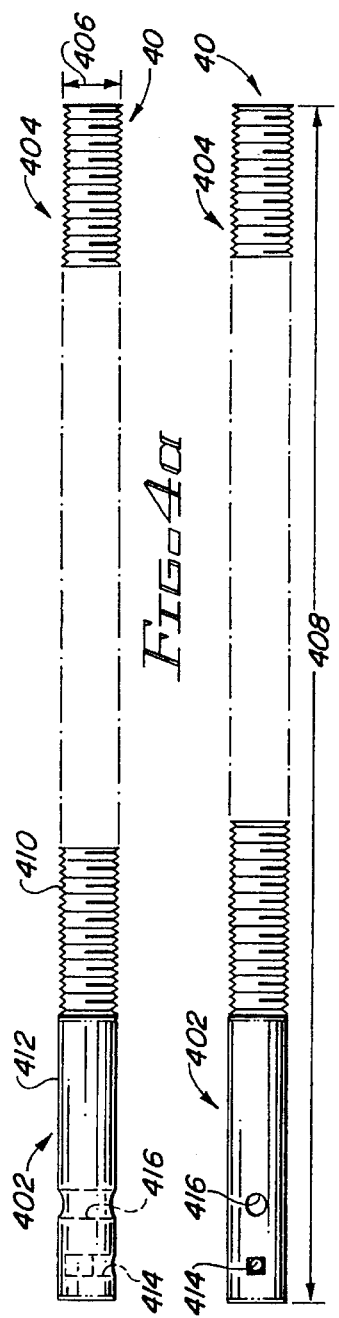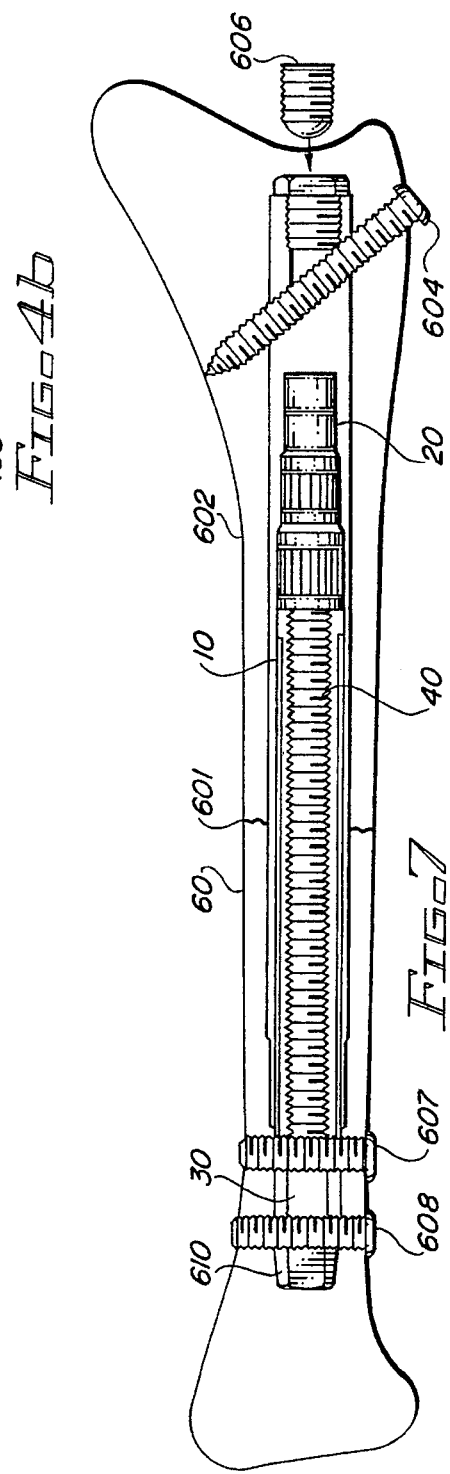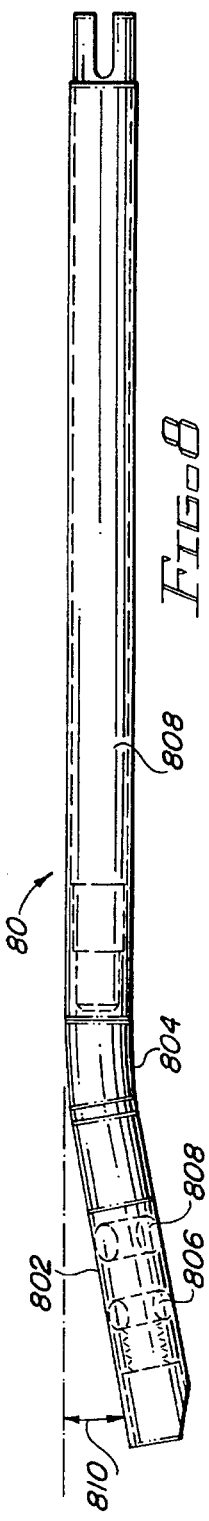

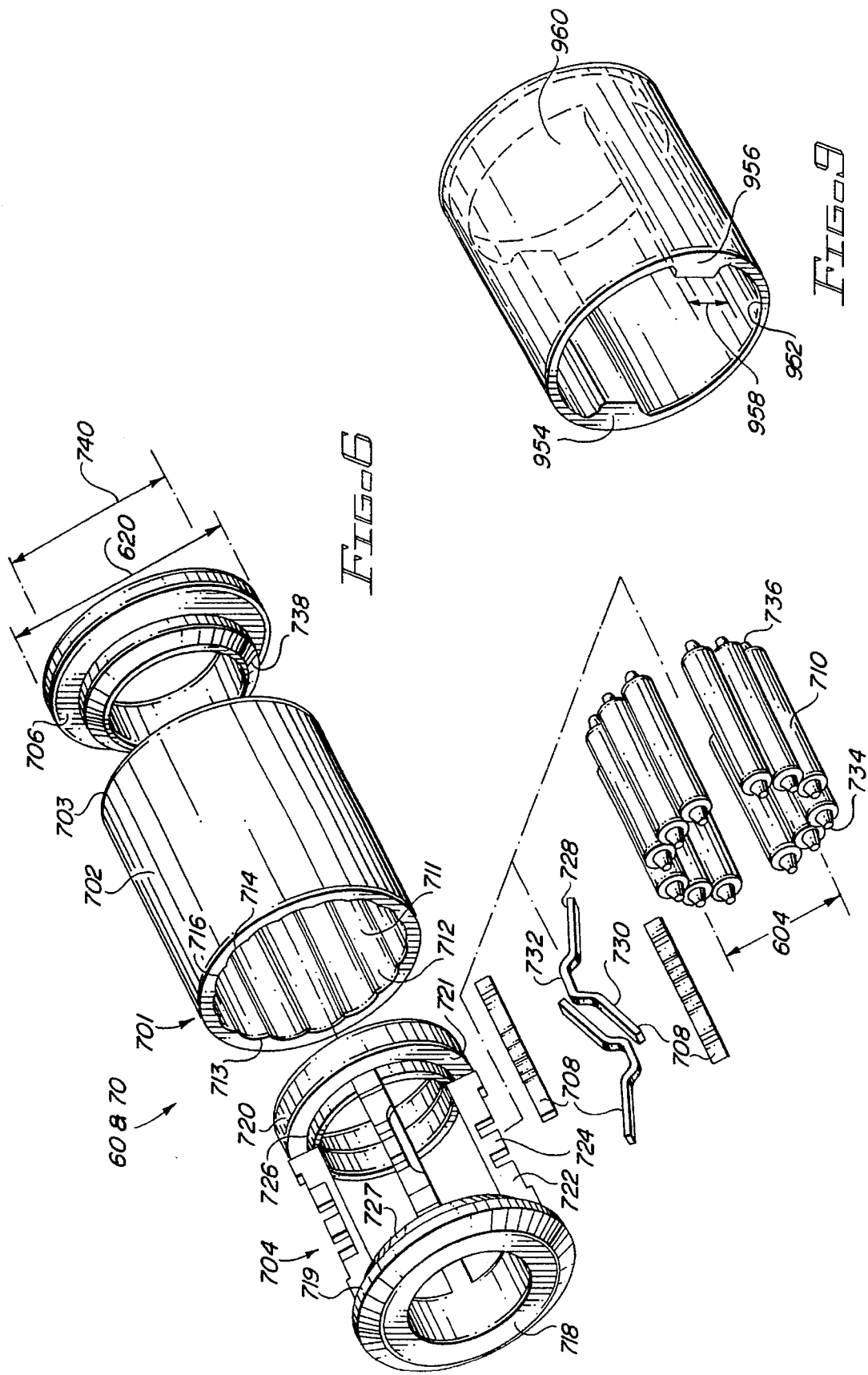

INTRAMEDULLARY SKELETAL DISTRACTOR AND METHOD

BACKGROUND OF THE INVENTION

1. Field of the Invention

The present invention relates generally to surgical implements for use in the lengthening of bones, and more specifically to an apparatus and method for intramedullary skeletal distraction.

2. Description of Related Art

The problem of limb-length discrepancies resulting from congenital, postinfectious, and post-traumatic disorders is one that has received the attention of many researchers. Various devices have been known in the art that can be attached to the ends of a sectioned bone and made to lengthen progressively, the lengthening causing growth of bone tissue at the site of sectioning and thus a commensurate lengthening of the bone. The devices are then removed when the desired length is achieved or they may be left in place as an internal splint.

External distractors, usually comprising pins passing through soft tissue and bone, can carry non-negligible potential risks of infection, pain, and muscle contractures. One benefit, however, is the accessibility of this type of device to manipulation extracutaneously.

Several internal apparati, designed to be placed within the medulla of a long bone, have been described. Two intramedullary devices for the fixation of bone fractures have been described by Roalstad et al. (U.S. Pat. No. 4,262,665) and Raftopoulos et al. (U.S. Pat. No. 4,453,539). Both devices include a threaded member and a cooperating screw positioned to hold the two ends of a broken bone together and permit them to unite and heal the fracture.

Intramedullary elongation devices have also been described in prior publications. Westerhoff (U.S. Pat. No. 4,157,715) teaches the use of osmotic pressure and a return-motion stop to effect a one-way telescoping of a pair of cylindrical members. Sirash (U.S. Pat. No. 4,384,373), Moore et al. (U.S. Pat. No. 4,502,160), and Kotz et al. (U.S. Pat. No. 4,892,546) all describe prostheses designed to elongate in response to an external adjustment; that is, an additional procedure must be undergone to lengthen the device, typically the rotation of a screw to telescopically elongate a pair of interconnected members such as a cylinder and a rod.

An attempt to obviate the need for directly contacting the elongation members has been made by Grammont et al. (U.S. Pat. No. 5,074,882; Trans. 37th Ann. Mtg. Orthopaedic Research Soc., Vol. 16, p. 657, 1991). As in previous prostheses, two telescoping tubes are used to stimulate progressive elongation of a limb. However, in this device no invasive procedure is necessary; rather, an internal ratchet mechanism responsive to a limb rotation of 20 degrees is incorporated. Since the ratchet mechanism utilizes intermeshing teeth, the minimum amount of rotation necessary to engage the ratchet is limited by the number of teeth that can be disposed about the bush. When the limb is manipulated in the appropriate direction, either by the patient or by another person, the internal ratchet mechanism permits a threaded screw to move linearly, translating one part of the device relative to another and thereby creating elongation of the device. When the limb is turned in the opposite direction, the screw does not advance linearly, and no longitudinal movement is permitted.

SUMMARY OF THE INVENTION

The present invention, an intramedullary skeletal distractor for use in a medullary cavity of a bone, comprises a first and a second cylindrical member dimensioned such that the second cylindrical member can slide into the first in telescopic fashion. Each member has a first end, a second end, and a bore, and the members are telescoped such that the first end of the second member is positioned between the first and second ends of the first member. In use, the first and second cylindrical members are attached to the proximal and distal sections of a bone, respectively.

The device further comprises an elongated rod, also having a first and a second end, with a diameter dimensioned to slide within the bore of the second cylindrical member. The first end of the rod resides within the bore of, and is affixed to, the first cylindrical member. The second end of the rod resides within the bore of the second cylindrical member.

Clutch means are positioned within the bore of the first cylindrical member upon the elongated rod. The clutch means are selectively responsive to rotation in a first direction, upon which it operates upon the second cylindrical member to effect elongating telescopic movement. Upon rotation in the opposite second direction, the clutch means locks the rod from rotating and thus prevents contracting telescopic motion.

Specifically, the clutch means comprises a first and a second clutch. The first clutch is positioned in the bore of the first cylindrical member between the first ends of the first and second cylindrical members. The first clutch has an outer periphery dimensioned to fit sufficiently tightly in the bore that movement is communicated between the first cylindrical member and the first clutch. The first clutch is also positioned upon the elongated rod and is constructed so that the inner diameter of the first clutch fits sufficiently tightly thereupon that motion in the second direction is communicated thereto and that motion in the first direction permits slippage therebetween.

The second clutch is positioned within the bore of the second cylindrical member and upon a threaded portion of the elongated rod. The second clutch also has an outer periphery dimensioned to fit sufficiently tightly in the bore that movement is communicated therebetween. When rotation of the elongated rod occurs in the second direction, slippage of the elongated rod within the second clutch is permitted, and the second clutch travels along the threaded portion, pushing the second cylindrical member away from the first cylindrical member. When rotation occurs in the first direction, slippage of the elongated rod within the second clutch is not permitted, the elongated rod rotates with the second clutch, slipping within the first clutch, and no lateral motion occurs.

In order to prevent excessive lengthening within a particular time period, an indicator mechanism is further provided to prevent elongation beyond a predetermined amount. This indicator mechanism permits the predetermined amount of elongation and then imposes a resistance to further elongation. The force needed to overcome this resistance exceeds the force that would be exertedunder normal conditions upon the limb. In order to overcome the resistance of the indicator, an external manipulation is necessary in the form of a torque applied to the limb. An audible sound is emitted from the indicator when sufficient torque has been applied, providing a cue that the next cycle of progressive elongation can begin. In a typical human subject, the predetermined amount of elongation is approximately 0.25 mm per quarter day, resulting in a 1 mm/day elongation.

The method of using the above-described skeletal distractor comprises the following steps: The device is inserted into the medullary canal of a bone. The first cylindrical member is then affixed to the proximal section of bone, and the second cylindrical member, to the distal section of bone. Due to the precision of the clutch mechanism used herein, during the normal motions of daily life, sufficient torsion will typically occur to activate the clutch mechanism and effect elongation. In order to prevent excessive elongation, the indicator mechanism prevents further elongation when a predetermined lengthening has occurred. To reactivate the device, as previously described, a torque is applied to the limb until the audible sound is emitted, indicating that elongation may begin again. When sufficient elongation has occurred in the bone, the device is removed.

Alternatively the indicator may be designed so that upon sufficient torque being applied, the resistance is overcome, and the device is free to rotate until the audible sound is heard. Then the elongated rod is locked against further movement until the next forcible manipulation.

It is thus an object of the invention to provide an intramedullary skeletal distractor that elongates under the normal forces and torsions experienced in daily life and thus stimulates progressive elongation of a sectioned bone.

It is a further object of the invention to provide a device that has no extracutaneous elements.

It is yet another object of the invention to provide an elongation mechanism whose motion is effected with the use of a pair of clutches and a threaded rod that together cause elongationunder rotation in one direction and prevent shortening under rotation in the opposite direction.

Another object of the invention is to provide a method for elongating a bone that comprises inserting a distractor responsive to rotational oscillations during normal movement within the medullary canal of a bone, affixing the telescoping elements to the two ends of the bone, and permitting the elements to elongate a determined amount per unit time.

The features that characterize the invention, both as to organization and method of operation, together with further objects and advantages thereof, will be better understood from the following description used in conjunction with the accompanying drawing. It is to be expressly understood that the drawing is for the purpose of illustration and description and are not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 illustrates the skeletal distractor (a) assembled and in its most shortened position and (b) in exploded view.

FIG. 2 is (a) a longitudinal view and (b) a longitudinal sectional view of the first cylindrical member. The views in (a) and (b) are rotated 90 degrees from each other along the cylindrical axis.

FIG. 3 is (a) a longitudinal view and (b) a longitudinal section view of the second cylindrical member. The views in (a) and (b) are rotated 90 degrees from each other along the cylindrical axis.

FIG. 4 illustrates the elongated rod. The views in (a) and (b) are rotated 90 degrees from each other along the cylindrical axis.

FIG. 6 depicts an exploded view of the overrunning roller clutch used in the distractor.

FIG. 7 illustrates the skeletal distractor positioned within the medullary cavity of a bone.

FIG. 8 illustrates an alternate embodiment of the device having a bent first cylindrical member.

FIG. 9 is a perspective view of the keyring of the present invention.

DETAILED DESCRIPTION OF THE PREFERRED EMBODIMENTS

Figure 5C:
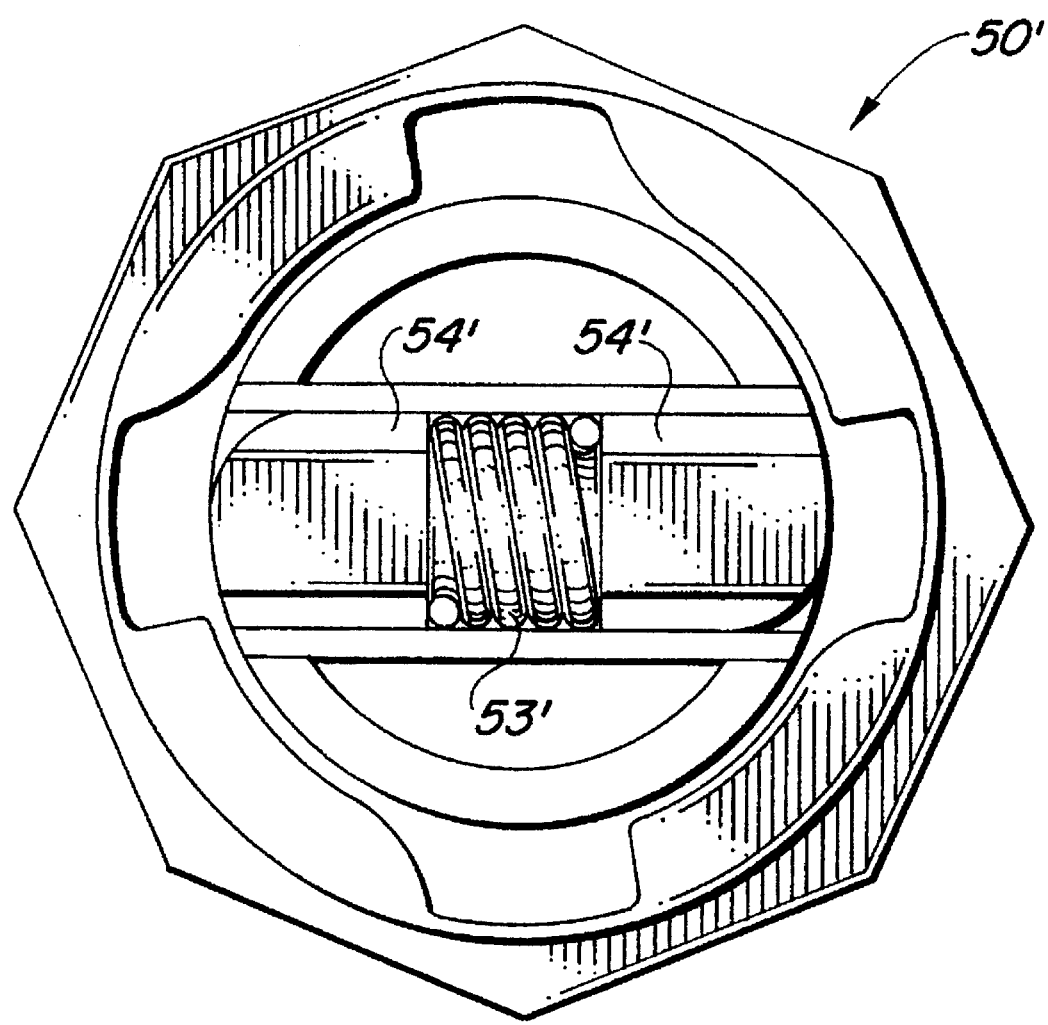
FIG. 5 (a) and (b) are cross-sectional views of two embodiments of the indicator mechanism with the piston (a) within the cutout and (b) entirely within the bore in the elongated rod.

The preferred embodiments of the present invention will now be discussed with reference to FIGS. 1–9.

The intramedullary skeletal distractor, shown assembled and in exploded view in FIG. 1, will be referred to generally by the reference numeral 10. Device 10 comprises a first 20 and a second 30 cylindrical member, shown in cross section in FIGS. 2 and 3, respectively, an elongated rod 40, shown in FIG. 4, and an indicator mechanism 50, shown in FIG. 5. In this embodiment the clutch means comprise a first clutch 60 and a second clutch 70 (FIG. 1), both overrunning roller clutches that permit rotation in one direction and lock movement in the other direction. It can be appreciated by one skilled in the art that other types of clutches may be substituted, such as spring, friction, magnetic, or sprag clutches.

In detail, first cylindrical member 20 (FIG. 2) has a first end 202, a second end 204, an outer diameter 206, an inner wall 14, and outer wall 216, and a partial longitudinal bore 208. Bore 208 communicates with second end 204 but does not proceed through to first end 202.

Adjacent first end 202 is angled bore 212, through which a screw 604 is inserted to anchor first cylindrical member 20 to a proximal section 602 of bone 60 (see FIG. 7). Angled bore 212 does not communicate with longitudinal bore 208. In the preferred embodiment, angle 218, measured from the cylinder axis of first end 202 to the axis of bore 212 is in the range of 45–60 degrees for the case of, for instance, a femur or a humerus. This angle permits the anchoring means to engage the thickest portion of bone and thus provide the greatest strength.

For the case of a tibia, a slightly different embodiment of first cylindrical member 80 is provided. As shown in FIG. 8, first end 802 of first cylindrical member 80 is slightly bent, typically at an angle 810 of approximately 10 degrees from the cylinder axis. The location of the bend 804 occurs between the first end 802 and the end of bore 808 closest the first end 802. In this embodiment, instead of angled bore 212, two diametric bores 806 and 808 are provided adjacent first end 802 through which a pair of screws may be inserted to anchor first cylindrical member 80 to the proximal section of the tibia.

Returning to FIG. 2, within first end 202 and communicating with angled bore 212, but not communicating with longitudinal bore 208, is threaded longitudinal bore 210. Threaded bore 210 is utilized during insertion and retrieval of the device by threading an extension member (not shown) into bore 210. Bore 210 is also used as a passageway for the insertion of a drill guide to assist in the correct placement of screw 604 (see also FIG. 7). In an alternate embodiment, a nail may be used in place of screw 604. With either a screw or a nail, bore 210 may also be used for a locking set screw 606 to secure the screw or the nail in place.

Bore 208 has three stages, which, proceeding from second end 204, are first section 220, having the largest diameter 222 and a length 221; second section 224, having intermediate diameter 226; and third section 228, having the smallest diameter 230 and having an octagonal internal wall profile in axial cross section.

Outer wall 216 has a tapered section 232 at second end 204, through which is a pair of opposed slots 234 and 236, having a width 238 for engaging keyring 95, to be discussed in the following.

Second cylindrical member 30, shown in detail in FIG. 3, has first end 302, second end 304, outer diameter 306, longitudinal bore 308, outer wall 310, and inner wall 312. Outer diameter 306 is dimensioned to slidably engage first section 220 of bore 208 in first cylindrical member 20. Outer diameter 306 is further dimensioned to be larger than the diameter 226 of second section 224; therefore, the depth to which second cylindrical member 30 can be inserted into first cylindrical member 20 is determined by the length 221 of first section 220. when assembled (see FIG. 1), first end 302 is inserted (after elongated rod 40, vide infra) into bore 208 from second end 204 of first cylindrical member 20. In the preferred embodiment, second end 304 is tapered 315 and has a rounded edge 313 to facilitate insertion. A pair of opposed slots, 314 and 316, not communicating with bore 308, run from adjacent second end 304 to a section 318 of first end 302. Slots 314 and 316 have a width 315 perpendicular to the axis of second cylindrical member 30. Near second end 304 is a pair of diametric bores 320 and 322, proceeding through and having a larger diameter than the width 315 of slots 314 and 316. Bores 320 and 322 are utilized for screws 607 and 608, which secure member 30 to a distal section 610 of bone 60 (see FIG. 7).

Beginning from the second end 304, bore 308 has three stages: first section 334, having diameter 326; second section 336, which is threaded, having diameter 338; and third section 340, having diameter 342.

Distal plug 90 [FIG. 1(b)] is dimensioned to fit into bore 308 of the second cylindrical member 30 at second end 304 and extends from second end 304 past the location of bore 320. Distal plug 90 serves to strengthen the distal end and to block intramedullary tissue from entering bore 308 during insertion and elongation. Distal plug 90 also has a pair of diametric bores 902 and 904 extending therethrough and communicating with bores 322 and 320, respectively.

Keyring 95 (FIG. 9) is a cylindrical member dimensioned to be press fit onto the second end 204 of first cylindrical member 20. Keyring 95 has an inner wall 952, from which a pair of opposed protrusions 954 and 956, each having a width 958, extend into bore 960. When assembled, protrusions 954 and 956 engage opposed slots 234 and 236 in first cylindrical member 20 and also opposed slots 314 and 316 in second cylindrical member 30. The purpose of keyring 95 is to prevent excessive rotation of first 20 and second 30 cylindrical members and yet permit sufficient relative rotation to activate the clutches. Thus, the width 958 of protrusions 954 and 956 must be dimensioned smaller than slot widths 238 and 315 to permit a relative rotation sufficient to activate the clutch mechanism and is also within the limits of natural anatomical limb rotations. In the preferred embodiment, a rotation of 3 degrees is permitted.

Elongated rod 40, shown in FIG. 4, has a first end 402, and second end 404, length 408, and diameter 406. Extending from second end 404 is threaded portion 410 of rod 40, dimensioned to mate with threaded section 336 of second cylindrical member 30. Extending from first end 402 is nonthreaded portion 412. Extending into nonthreaded portion 412 are partial 414 and full 416 diametric bores. When assembled (see FIG. 1), first end 402 resides within the full extent of bore 208 of first cylindrical member 20 and is threaded into threaded section 336 of second cylindrical member 30, with which it is rotatably engaged and longitudinally extendable thereby, as will become apparent in the following.

Affixed to nonthreaded portion 412 of elongated rod 40 at first end 402 is indicator mechanism 50 (see FIG. 1), shown in detail in FIG. 5. Indicator mechanism 50 comprises indicator housing 52, piston 54, and spring 53.

Indicator housing 52 is a hollow octagonal element having an outer periphery 520 dimensioned to closely fit within third section 228 of bore 208 of first cylindrical member 20. Indicator housing 52 also has a bore 522 that has four substantially identical cutouts 526 that are equally spaced radially (at 90 degrees from each other) about bore 522, cutouts 526 having a radial extent 528. Bore 522 further has a minimum diameter 524 over the bore 522 regions away from cutouts 526. Minimum diameter 524 is dimensioned to encompass and closely engage nonthreaded portion 412 of elongated rod 40.

Piston 54 and cutouts 526 are shaped so as to closely engage each other. The radial profile 542 of piston 54 has a sloping edge 544 and a substantially straight edge 546 approximately collinear with the radius of elongated rod 40. The radial extent 548 of pistons 54 is greater than the radial extent 528 of cutouts 526. Cutouts 526 have a radial profile 541 having a sloping edge 543, which curves oppositely from curve 544, and a substantially straight edge 545. The sloping and straight edges of the piston and a cutout substantially align when the piston resides within the cutout.

When assembled (see FIG. 1(b)), spring 53 is inserted into bore 414 in rod 40 and piston 54 is inserted into bore 414 atop spring 53. Indicator housing 52 is then fit over first end 402 of rod 40 so that piston 54 resides in one cutout 526 and extends partially into bore 414. It can be seen that relative rotation between indicator housing 52 and rod 40 is opposed in a first direction 548 toward straight edge 546, but that it is possible in a second direction 549 toward sloping edge 544. If rotation in second direction 549 is to occur, however, a sufficient torque must be exerted to overcome the coefficient of friction of the mechanism and the spring constant of spring 53, so that spring 53 is compressed by piston 54 being pushed into bore 414. When sufficient rotation in the second direction occurs so that pistons 54 reside completely within bore 414, as shown in FIG. 5(b), less torque is required to continue rotation. When a rotation of 90 degrees is achieved, piston 54 reaches the next cutout 526, and an audible sound is emitted as piston 54 snaps into cutout 526 as spring 53 is released.

In an alternate embodiment, an audible sound may be a signal that sufficient forcible torque has been applied to overcome the resistance of the indicator mechanism and thus alert the patient that progressive elongation may occur.

In another embodiment, a magnetic field may be applied to move the piston into the bore 714, releasing the indicator mechanism.

In a further embodiment, the indicator mechanism comprises a pair of opposed pistons and a full diametric bore extending completely through the elongated rod. In this configuration, the spring is held within the bore by the pair of pistons. The housing and the elongated rod rotate relatively to each other as previously described in the second direction from one pair of opposed cutouts to an adjacent pair of opposed cutouts.

It can be seen that further embodiments may comprise different numbers of cutouts, also equally radially spaced. For instance, three cutouts would be spaced 120 degrees apart. Having the flexibility afforded by such a variety of indicator mechanisms permits one to custom design elongation parameters without altering any of the other elements.

Also affixed to nonthreaded portion 412 of elongated rod 40 is indicator bearing 55, a cylindrical member having a longitudinal bore 552 dimensioned to closely engage nonthreaded portion 412 (see FIG. 1). Diametric bore 554 communicates with bore 416, and locking pin 58 is inserted through bores 554 and 416, retaining bearing 55 upon rod 40. When assembled, bearing 55 resides within third section 228 of bore 208 in first cylindrical member 20, further toward second end 204 than and adjacent to indicator mechanism 50.

First clutch 60, the structure of which is shown in FIG. 6, has an outer periphery 620 dimensioned to fit sufficiently tightly within the second section 224 of bore 208 of first cylindrical member 20 that rotational motion can be communicated therebetween. First clutch 60 further has an inner diameter 604 dimensioned to closely engage nonthreaded portion 412 of elongated rod 40 and also communicate rotational motion therebetween. When assembled, first clutch 60 is mounted on nonthreaded portion 412 between indicator bearing 55 and threaded portion 410. First clutch 60 permits slippage between rod 40 and first cylindrical member 20 when rotation occurs in a first direction and communicates rotation therebetween in the second direction.

Second clutch 70, identical in structure to first clutch 60 shown in FIG. 6, has an outer periphery 702 dimensioned to fit sufficiently tightly within widest section 340 of second cylindrical member 30 that rotational motion can be communicated therebetween. Second clutch 70 further has an inner diameter 740 dimensioned to engage threaded portion 410 of rod 40 and move longitudinally therealong. The directionality of second clutch 70 permits locking between rod 40 and second cylindrical member 30 when rotation occurs in the first direction; rotation in the second direction causes rotational slip, thus allowing linear movement between rod 40 and member 30. When the device 10 is fully assembled, rotation in the second direction causes second clutch 70 to move along threaded portion 410 of rod 40 toward second end 404, and consequently threaded portion 410 moves in a longitudinal direction out of threaded section 336 of bore 308 in second cylindrical member 30. Such relative longitudinal movement serves to push second cylindrical member 30 out of the bore 208 of first cylindrical member 20, elongating device 10.

In detail, clutches 60 and 70 comprise cylindrical clutch housing 702, clutch cage 704, end cap 706, four clutch springs 708, and twelve clutch rollers 710.

Clutch housing 702 has a bore 711 having inner surface 712, a first end 701, and a second end 703. Inner surface 712 has sixteen asymmetrically shaped radial cutouts 713 having a gradual slope 714 in a first direction and a sharper slope 716 in a second direction.

Clutch cage 704 comprises a first ring-shaped end 718 and a second ring-shaped end 720 spaced apart by four equally spaced support members 722 affixed to the facing surfaces 719 and 721 of ends 718 and 720, respectively. Each of these facing surfaces 719 and 721 has a circumferential channel 726 and 727, respectively, therein. Second end 720 is dimensioned to slide within first end 701 of clutch housing 702; first end 718 is larger than clutch housing 702 and thus will not slide past first end 701 of clutch housing 702.

Each clutch roller 710 comprises a substantially cylindrical member having a first 734 and a second 736 narrowed end. One set of three clutch rollers 710 resides between adjacent support members 722, the first ends 734 positioned within channel 727 and the second ends 736 positioned within channel 726. When assembled, with cage 704 within housing 702, clutch rollers 710 are biased against sharper slope 716 by springs 708, which are mounted on support members 722. Rollers 710 cannot rotate in the second direction past the sharper slope 716 of the housing, but they can rotate in the first direction past the gradual slope 714. This selective rotational ability provides the clutch directionality.

To complete the assembly, end cap 706, having a depending lip 738 dimensioned to fit within housing bore 711, is placed over housing 702 at second end 703.

Since both clutches 60 and 70 are overrunning roller clutches, very small rotations can effect elongation. In practice, torsions as small as 1 degree, well within the range of normal physiological movement, will cause elongation of device 10. Therefore, no external manipulation is necessary, and, rather than the several larger elongations per day required of previously disclosed devices, small progressive longitudinal increments can occur throughout the day, a more desirable situation for stimulation of bone growth. The only external manipulation required is that necessary to release the indicator mechanism 50. In practice, for human subjects, the device is designed to permit 0.25 mm of elongation per 90 degree rotation of the elongated rod 40, and manipulation to release this mechanism is recommended four times per day, for a total elongation of 1 mm per day.

The method of utilizing the above-described device comprises the following steps (see FIG. 7): An incision at the head of the sectioned bone 60 to be treated is made, through which the distractor 10 is inserted into the medulla of the bone. The first 20 and the second 30 cylindrical members are affixed by screws 604, 607, and 608 to the proximal 602 and distal 610 sections of the bone 60, respectively when any torsional movement in the first direction occurs, the second clutch moves along the threaded portion of the elongated rod, pushing the second cylindrical member away from the first, elongating the device. Successive rotations continue to telescope the device until 0.25 mm elongation is reached, at which point the indicator mechanism locks against further elongation. At the end of a quarter-day, either a second party or the patient him/herself forcibly rotates the limb until the piston is pushed within the bore in the elongated rod and clutch movement can occur again. When the limb has been stimulated to grow at bone section point 601 to the length desired, the distractor is removed from the bone 60 or left in place as an internal splint.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. An intramedullary skeletal distractor for use in a medullary cavity of a bone, comprising:

a first and a second cylindrical member, each having a first end, a second end, and a bore, the second cylindrical member dimensioned to slidingly telescope into the first cylindrical member;

an elongated rod having a first end and a second end and further having a diameter dimensioned to slide within the bore of the second cylindrical member, the first end of the rod residing within the bore of the first cylindrical member and affixed to the first cylindrical member and the second end of the rod residing within the bore of the second cylindrical member; and clutch means responsive to rotation positioned in surrounding relation to the elongated rod within the bore of the first cylindrical member, the clutch means rotatable in a first direction and lockable in a second direction, the clutch means further operable upon the second cylindrical member to effect elongating telescopic movement of the first and the second cylindrical members upon rotation in the first direction, the elongation effectable with rotations in the first direction generally equal to or greater than 1 degree, wherein the clutch means comprises:

a first clutch positioned between the first ends of the first and second cylindrical members, having an outer diameter dimensioned to fit sufficiently tightly within the bore of the first cylindrical member that movement is communicated therebetween and further having an inner diameter dimensioned to fit in sufficiently close relation with the elongated rod that rotation of the first cylindrical member in the second direction effects rotation of the elongated rod and rotation of the first cylindrical member in the first direction permits slippage with the elongated rod; and a second clutch positioned within the bore of the second cylindrical member, having an outer diameter dimensioned to fit sufficiently tightly within the bore of the second cylindrical member that movement is communicated therebetween and further having an inner diameter dimensioned to fit in sufficiently close relation with the elongated rod that rotation of the first cylindrical member in the first direction effects rotation with respect to the elongated rod and rotation of the first cylindrical member in the second direction permits slippage with the elongated rod, the second cylindrical member further having means for moving with respect to the elongated rod, rotation in the second direction causing the second clutch and the second cylindrical member to move relative to the elongated rod and in an outward direction relative to the first cylindrical member and thereby effect elongating telescopic movement.

2. The distractor recited in claim 1, further comprising:

means for attaching the first cylindrical member to a proximal section of a bone; and means for attaching the second cylindrical member to a distal section of a bone.

3. The distractor recited in claim 2, wherein:

the bore in the first cylindrical member comprises a partial longitudinal bore extending from the second end to a point at a distance from the first end of the first cylindrical member;

the first cylindrical member has an angled bore adjacent the first end, the angled bore passing through the first cylindrical member at a location proximal of the partial longitudinal bore, the angled bore dimensioned to receive said attaching means for engaging the proximal section of a bone and the angled bore; and the second cylindrical member has a diametric bore adjacent the second end, the diametric bore having a diameter dimensioned to receive said attaching means for engaging the distal section of a bone and the diametric bore.

4. The distractor recited in claim 3, further comprising a distal plug for strengthening and for blocking tissue from entering the second end of the second cylindrical member, the distal plug having:

a diameter dimensioned to fit snugly into the bore of the second cylindrical member at the second end;

a length dimensioned to extend from the second end of the second cylindrical member beyond the diametric bore; and a diametric bore having a diameter substantially equal to the diameter of and communicating with the diametric bore in the second cylindrical member.

5. The distractor recited in claim 3, wherein the first cylindrical member further has a threaded longitudinal bore extending from the first end to the angled bore dimensioned to receive a set screw for securing anchoring means placed in the angled bore.

6. The distractor recited in claim 2, wherein:

the bore in the first cylindrical member comprises a partial longitudinal bore extending from the second end to a bore end located at a distance from the first end; and the first cylindrical member is bent at the first end at an angle, the bend placed between the first end and the bore end.

7. The distractor recited in claim 6, wherein the first cylindrical member has a diametric bore adjacent the first end, the diametric bore having a diameter dimensioned to receive anchoring means for engaging the proximal section of a bone and the diametric bore.

8. The distractor recited in claim 1, wherein the elongated rod has threads at the second end and the means for moving comprises means for engaging and moving along the threads.

9. The distractor recited in claim 8, wherein the first and the second clutches comprise a first and a second overrunning roller clutch.

10. The distractor recited in claim 9, wherein the first and the second overrunning roller clutches are responsive to a rotation greater than or equal to 1 degree.

11. The distractor recited in claim 1, further comprising an indicator mechanism mounted on the elongated rod that permits elongation to a predetermined amount and locks upon reaching the predetermined amount and that is further releasable by forcible external manipulation.

12. The distractor recited in claim 1, wherein:

the first end of the elongated rod has a diametric bore therethrough; and the indicator mechanism comprises:

a spring inserted into the diametric bore in the elongated rod;

two substantially identical pistons, one inserted into each end of the diametric bore in the elongated rod, each piston having a radial profile that comprises a sloping edge in the first direction and a substantially straight edge collinear with a radius of the elongated rod in the second direction; and a generally cylindrical indicator housing having a bore having a minimum diameter dimensioned to encompass and closely engage the first end of the elongated rod and further having an outer periphery dimensioned to closely fit within the bore of the first cylindrical member, the bore of the indicator housing further having a plurality of equally radially spaced cutouts, the profile of the cutouts being substantially identical to the radial profile of the pistons, wherein the pistons are movable in the second direction from a first position in which the pistons each reside within a cutout to a second position in which the pistons are moved within the bore in the elongated rod, compressing the spring, and wherein rotation in the first direction from the first position is opposed by the straight edge of the indicator housing cutout abutting the straight edge of the piston.

13. The distractor recited in claim 1, the second end of the second cylindrical member further having a tapered portion and a rounded edge to facilitate insertion into the bone.

14. The distractor recited in claim 1, further comprising means for limiting the relative rotation between the first and the second cylindrical members.

15. The distractor recited in claim 14, wherein:

the first cylindrical member has a tapered section at the second end, the tapered section having a diameter, and a pair of opposed slots having a width and a length; and the second cylindrical member has a pair of opposed slots extending from adjacent the second end to a section of the first end, the slots having a radial depth insufficient to communicate with the bore of the second cylindrical member, the slots further having a width, the slots further in communication with the slots in the first cylindrical member; and the limiting means comprises a cylindrical keyring having:
  a bore dimensioned to closely surround the second end of the first cylindrical member;
  an inner wall; and
  a pair of opposed protrusions extending from the inner wall into the bore, the protrusions having a radial depth sufficient to engage the slots in the first and the second cylindrical members, and further having a width dimensioned smaller than the width of the slots in the second cylindrical member; and wherein the difference between the width of the protrusions and the width of the slots in the second cylindrical member defines a maximum relative rotation permitted between the first and the second cylindrical members and further is sufficiently large to activate the clutch means.

16. The distractor recited in claim 15, wherein the difference between the width of the protrusions and the width of the slots in the second cylindrical member permits a maximum relative rotation of 3 degrees.

17. The distractor recited in claim 1, further comprising means for limiting the relative lengthening between the first and the second cylindrical members.

18. The distractor recited in claim 17, wherein the first cylindrical member has a tapered section at the second end, the tapered section having a diameter, and a pair of opposed slots having a width and a length; and the second cylindrical member has a pair of opposed slots extending from adjacent the second end to a section of the first end, the slots having a radial depth insufficient to communicate with the bore of the second cylindrical member, the slots further having a width, the slots further in communication with the slots in the first cylindrical member; and the limiting means comprises a cylindrical keyring having:
  a bore dimensioned to closely surround the second end of the first cylindrical member;
  an inner wall; and
  a pair of opposed protrusions extending from the inner wall into the bore, the protrusions having a radial depth and a width sufficient to engage the slots in the first and the second cylindrical members; and wherein the length of the slots in the second cylindrical member defines a maximum relative lengthening permitted between the first and the second cylindrical members, the protrusions permitting elongating telescopic movement between the first and the second cylindrical members until the protrusions abut the section of the first end of the second cylindrical member at which the slots terminate.

* * * * *